United States Patent [19]
Hiraga et al.

[11] 3,953,483
[45] Apr. 27, 1976

[54] 17-NOR-6-METHYL-STEROIDS

[75] Inventors: Kentaro Hiraga, Nagaokakyo; Kouichi Yoshioka, Ukyoku; Giichi Goto, Toyonaka; Ryo Nakayama, Kawanishi; Michio Masuoka, Miki, all of Japan

[73] Assignee: Takeda Chemical Industries, Ltd., Osaka, Japan

[22] Filed: June 13, 1974

[21] Appl. No.: 479,676

[30] Foreign Application Priority Data
June 16, 1973 Japan............................. 48-68107

[52] U.S. Cl. ................... 260/397.3; 260/397.4; 260/397.5; 424/242
[51] Int. Cl.² ............................................. C07J 1/00
[58] Field of Search ........................... 260/397.3

[56] References Cited
UNITED STATES PATENTS

| 2,739,974 | 3/1956 | Colton | 260/397.3 |
| 3,117,966 | 1/1964 | Petrow | 260/239.55 |
| 3,127,396 | 3/1964 | Wiechert et al. | 260/239.5 |
| 3,356,694 | 12/1967 | Lunn | 260/397.3 |
| 3,497,498 | 2/1970 | Georgian | 260/239.55 |
| 3,655,649 | 4/1972 | Habermehl et al. | 260/239.5 |
| 3,679,715 | 7/1972 | Beaton et al. | 260/397.1 |

OTHER PUBLICATIONS
Burn et al., Chem. and Ind., Nov. 3, 1962, pp. 1907–1908.
Fetizon et al., Chem. Abstracts, 58:14043f.

Primary Examiner—Ethel G. Love
Attorney, Agent, or Firm—Wenderoth, Lind & Ponack

[57] ABSTRACT

Novel steroid compounds are provided represented by the formula:

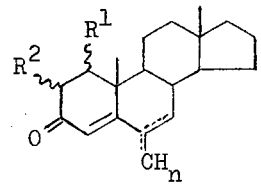

wherein each of $R^1$ and $R^2$ represents hydrogen or methyl group or $R^1$ and $R^2$ may be combined with each other to represent methylene group, n is 2 or 3 and the dotted line means a double bond at 6-exo-position when n is 2 or between 6- and 7-position when $n$ is 3.

These novel compounds show a strong anti-androgenic activity, especially by oral administration, and can be used as a remedy for the prostatomegaly.

4 Claims, No Drawings

17-NOR-6-METHYL-STEROIDS

The present invention relates to novel and useful steroid compounds and to a method for producing them, and more particularly to compounds of the formula:

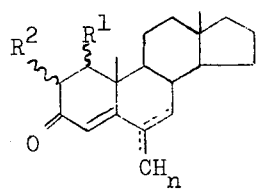
(I)

wherein each of $R^1$ and $R^2$ represents hydrogen or methyl group or $R^1$ and $R^2$ may be combined with each other to represent methylene group, $n$ is 2 or 3 and the dotted line means a double bond at 6-exo-position when $n$ is 2 or between 6- and 7-position when $n$ is 3.

The majority (about 70 %) of old men suffer from the prostatomegaly. They complain of dysuria (painful or difficult urination) and are exoposed to suffering from anuresis or uremia. However, there has not been developed an effective remedy for the prostatomegaly. Although a few compounds showing anti-androgenic activity were subjected to clinical tests, most of them could not provide a remedy for the aforesaid symptoms because of their severe side effcts such as marked atrophy of the adrenal gland, and thymus, as well as serious disorders in liver. Compounds showing anti-androgenic activity, for example, 17α-caproyloxy-19-norprogesterone causes 'fatty liver' as a side effect, and 16β-cyclohexyl-17β-hydroxyestr-4-en-3-one, 16β-ethyl-17β-hydroxyestr-4-en-3-one, 17β-acetyloxy-16β-ethylestr-4-en-3-one and so on are little effective by oral administration.

It has now been discovered unexpectedly that 17-position unsubstituted steroid compound (I) shows a strong antiandrogenic activity, especially by oral administration. The efficacy of compound (I) is about four times as strong as that of 17β-acetoxy-16β-ethylestr-4-en-3-one by oral administration. Furthermore, it has been found that compound (I) are not only substantially free from hormonal effects other than anti-androgenic one, but also free from considerable side effects in e.g. suprarenal gland, thymus, pituitary gland and liver, even after a long-term administration.

It is the principlal object of the present invention to provide the novel and useful compound (I).

Another object of the present invention is to provide a method for producing compound (I).

A further object is to provide new pharmaceutical compositions containing compound (I) and a method for employing compound (I) in the treatent of the prostatomegaly.

Other objects of the present invention and advantageous features thereof will become apparent as the description proceeds.

In this invention, compound (I) is produced by e.g. reacting the compound of the formula

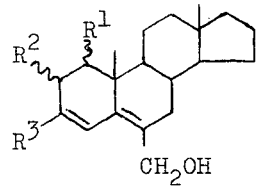
(II)

wherein $R^1$ and $R^2$ have the same meaning as above and $R^3$ stands for an alkoxy or acyloxy group, with an acid, followed by, upon necessity, isomerization. $R^3$ in compound (II) may be an alkoxy group, such as methoxy, ethoxy, propoxy or butoxy, or acyloxy group, such as acetoxy, propionoxy or benzoyloxy.

The acid to be used in this invention may be either a mineral acid, e.g. hydrochloric acid, sulfuric acid, nitric acid, phosphoric acid or carbonic acid, or an organic acid, e.g. acetic acid, oxalic acid, tartaric acid, benzoic acid or benzenesulfonic acid. This reaction is carried out under conditions which are generally used in the hydrolysis of 3-enol steroids. The reaction temperature ranges ordinarily from 60°C to 150°C and preferably from 85°C to 100°C. The reaction is carried to conclusion generally in 5 to 90 minutes and preferably in 10 to 30 minutes. The compound thus produced may, upon necessity, be subjected to isomerization in the form of reaction mixture in which it is present or alternatively after it has been isolated by means which are known per se.

This isomerization reaction is a reaction by which the double bond of the 6-exo-methylene group is shifted to 6-position to give a 6-methyl group, and this relocation of the double bond can be performed with ease, for example by causing a catalytic reduction catalyst to act upon the 6-exo-methylene compound (I). As said catalytic reduction catalyst, use may commonly be made of, for example, such metals as palladium, rhutenium, rhodium, platinum, nickel, cobalt, etc., either as they are or as supported on such suitable catalyst supports as carbon black, kaolin, quartz, pumice, zinc oxide, barium sulfate, glass fiber, asbestos, etc. It is desirable to employ these catalysts after causing a small amount of hydrogen to be adsorbed thereon or in conjunction with a hydrogen doner such as cyclohexene. The reaction is carried out in an organic solvent and can be hastened by heating. As said organic solvent, use is ordinarily made of alcohols such as methanol, ethanol, etc. but one may employ other common types of solvents which do not interfere with the particular reaction, such as tetrahydrofuran, dioxane, ethylacetate, benzene, etc. Further, if necessary, the reduction of the double bond can be inhibited by adding sodium acetate to the reaction system. The reaction conditions, e.g. temperature, pressure and time, are chosen according to the type of substrate compound, reaction procedure and the type of solvent to be employed.

When compound (II) is allowed to react with an acid in the presence of the catalytic reduction catalyst, no substantial occurrence of the 6-exo-methylene compound (I) is observed.

Compound (I) can be easily isolated and purified by means which are conventional per se, such as concentration, concentration under reduced pressure, crystallization, recrystallization, solvent extraction, pH adjustment, reextraction and chromatography.

The starting compound (II) may be prepared, e.g. according to the following reaction scheme;

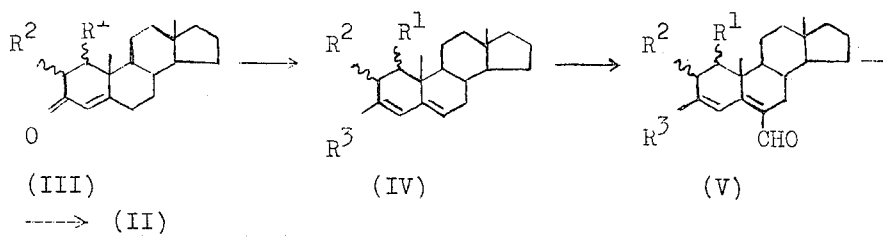

(III)  →  (IV)  →  (V)

----→ (II)

wherein $R^1$, $R^2$ and $R^3$ have the same meaning as above. Namely, a androst-4-en-3-one compound (III) is first reacted with an enolizing agent to obtain a 3-enol derivative (IV). Among the more common species of said enolizing agent are orthoformic acid esters (orthoformic acid alcohol esters) such as methyl orthoformate, ethyl orthoformate, propyl orthoformate, isopropyl orthoformate, etc.; Meerwein's reagent; acylating agents such as acid anhydrides e.g. acetic anhydride, propionic anhydride, etc., acid halide e.g. acetyl chloride, acetyl bromide, propionyl chloride, etc.; isopropenyl acetate; and so forth. These enolizing agents are preferably employed in a suitable solvent, examples of which are ethers such as tetrahydrofuran, dioxane, etc.; hydrocarbons such as benzene, toluene, etc.; and such basic solvents as pyridine, dimethylformamide, etc. If necessary, there may be allowed a catalyst to be present in the solvent. As said catalyst, use is commonly made of, for example, such acids as sulfuric acid, paratoluenesulfonic acid, etc. While ordinarily 1 to 2 moles of such an enolizing agent are used to each mole of compound (III), there may be employed two equivalents or more of said agent unless the reaction is thereby not inhibited. The reaction is conducted at room temperature, although the reaction temperature may be controlled, if necessary, by cooling or heating. The reaction time is 10 minutes or longer and, preferably, in the range of 20 to 40 minutes. After the reaction has been completed, the 3-enol derivative (IV) is isolated by means which are conventional per se, such as concentration, concentration under reduced pressure, crystallization, recrystallization, solvent extraction, pH adjustment, reextraction, chromatography, etc. Alternatively, one may dispense with the isolation and purification procedure and transfer the reaction product mixture containing the 3-enol derivative (IV) directly to the next reaction step. This 3-enol derivative (IV) is then reacted with a formylating agent to obtain a 6-formylandrosta-3,5-diene compound (V). The formylating agent to be used in this reaction can be any agent that is able to introduce a formyl group into the 6-position of the steroidal skeleton. Thus, use can be made, for example, of dimethylformamide, diethylformamide, methylphenylformamide or methylethylformamide and phosgene or phosphorus oxychloride; carbon monoxide and hydrogen chloride; formyl fluoride; dichloromethyl methyl ether; and so forth. Preferably, such a formylating agent is reacted with a 3-enol derivative (IV) in the proportion of 1 to 5 moles and, for better results, 1 to 2 moles to each mole of a 3-enol derivative (IV). The reaction can be conducted with or without using a solvent. The solvent which can thus be employed is chosen according to the types of substrate material and formylating agent. By way of example, use may be made, either alone or as a mixture, of methylene chloride, ethylene chloride, ethylene dichloride, anhydrous ethylene chloride, o-dichlorobenzene, ether, nitrobenzene, pyridine, trimethylamine, N-methylaniline, etc. If necessary, a catalyst such as aluminum chloride, copper chloride or boron fluoride, for instance, can be added. While the reaction ordinarily proceeds at room temperature, the reaction velocity can be controlled by cooling or heating. The reaction time depends upon other reaction conditions but generally it is desirable to carry the reaction to conclusion within about 20 to 30 minutes. The resultant 6-formylandrosta-3,5-diene compound (V) can be used as a raw material for the next step either as it is or after it has been isolated and purified by means which are conventional per se. The compound (V) thus obtained can then be converted with ease to the starting compound (II) by the reduction of the formyl group at 6-position of the steroid skeleton into a hydroxymethyl group. This reduction reaction can be conducted by suitable means, examples of which are reduction with a metal hydride such as sodium borohydride, lithium aluminum hydride, sodium aluminum hydride or trialkoxy lithium aluminum hydride and Meerwein-Pontdorf reduction. The reaction temperature, pressure and time and the type of solvent, among other conditions, can be selected according to the reduction procedure and the substrate material being employed. While the starting compound (II) can be easily isolated by routine separatory and purification procedures, it may be subjected, without prior isolation, to the next reaction.

Compound (I) has a strong anti-androgenic activity especially by oral administration and is free from other hormonal effects.

The following is the assay data on the anti-androgenic activity of 6-methylandrosta-4,6-dien-3-one (the test compound), a compound obtainable by the method of this invention. Testing procedure: Male rats of the SD-JCL strain, 21 days of age (body weights 40–55 g.) are castrated and, beginning on the next day, a daily dose of the test compound is suspended in 0.5 ml. of aqueous solvent and orally administered via a gastric catheter once daily, every day excepting Sundays, for a total of 10 times (12 days). Simultaneously with the administration of the test compound, a daily dose of 0.15 mg. of testosterone propionate is dissolved in 0.2 ml. of sesame oil and subcutaneously injected into the dorsal region of the neck.

On the day following the last day of administration, the rats are exsanguinated under ether anaesthesia and the seminal vesicles, ventral prostate and dorsal prostates are weighed. The anti-androgenic potency of the test compound is determined as follows. The percent inhibition by the test compound of the weight increases of these secondary sex structures caused by testosterone propionate is calculated by means of the equation given below and the percents thus obtained are used as indexes of anti-androgenic potency.

(Table 1)

$$\text{Percent inhibition (\%)} = \frac{\begin{bmatrix}\text{Weight for the group} \\ \text{dosed with testosterone} \\ \text{propionate alone}\end{bmatrix} - \begin{bmatrix}\text{Weight for the group} \\ \text{dosed with testosterone} \\ \text{propionate plus test} \\ \text{compound}\end{bmatrix}}{\begin{bmatrix}\text{Weight for the group} \\ \text{dosed with testosterone} \\ \text{propionate alone}\end{bmatrix} - \begin{bmatrix}\text{Weight for the group} \\ \text{dosed with solvent} \\ \text{alone}\end{bmatrix}} \times 100$$

Test results:

Table-1

| Dosage | | Number of rats | Weight of organs [average mg. ± standard error] | | |
|---|---|---|---|---|---|
| Testosterone propionate | Test compound | | Seminal vesicles | Ventral prostate | Dorsal prostate |
| 0 | 0 | 5 | 7±0.1 | 9±0.6 | 8±0.4 |
| 0.15mg. × 10 | 0 | 5 | 337±27 | 147±7 | 96±3 |
| 0.15mg. × 10 | 9.6mg. × 10 | 5 | 164±15 (53%) | 100±4 (34%) | 62±3 (38%) |
| 0.15mg. × 10 | 38.4mg. × 10 | 5 | 82±5 (77%) | 74±4 (53%) | 44±2 (59%) |

(%): Percent inhibition

As will be seen from the above results, this test compound significantly inhibits the weight increases of various secondary sex structures which are caused by the administration of testosterone propionate, the degree of inhibition (percent inhibition) being proportional to the dosage of the test compound. Thus, the above test results clearly demonstrate that this particular test compound has a potent anti-androgenic activity.

Thus, compound (I) is useful as drugs for the inhibition of the prostatomegaly and may be used for the treatment of hirsutism, acne, alopecia, Stein-Leventhal syndrome, etc. Dosage may be varied with symptoms of diseases to be treated, types of compound (I), hosts, administration form and so on, and e.g. is 40 to 300 milligrams per oral dose for adult human at the frequency of once a day to once a week depending upon symptoms.

Compound (I) can be administered in conventional dosage form such as tablet, pill, powder, granule, capsule, liquid, syrup, elixir, buccal, suspension, injection, etc. Some examples of practical formulations in which compound (I) of this invention is utilized as remedies for the prostatomegaly are as follows:

| Tablets: | 6-methylandrosta-4,6-dien-3-one | 50 mg. |
|---|---|---|
| | lactose | 100 mg. |
| | corn starch | 90 mg. |
| | sugar ester | 4 mg. |
| | calcium salt of carboxymethylcellose | 4 mg. |
| | magnesium stearate | 2 mg. |
| | | 250 mg/tablet. |

| Capsules: | 2α, 6-dimethylandrosta-4,6-dien-3-one | 5 mg. |
|---|---|---|
| | lactose | 140 mg. |
| | corn starch | 50 mg. |
| | sugar ester | 4 mg. |
| | calcium salt of carboxymethylcellose | 4 mg. |
| | magnesium stearate | 2 mg. |
| | | 250 mg/capsule |

| Injectables: | 1α,2-methylene-6-methylandrosta-4,6-dien-3-one | |
|---|---|---|
| | | 200 mg. |
| | benzyl benzoate | 20 cc. |
| | sesame oil | 1000 cc. |

It is to be understood that the following examples are solely for the purpose of illustration and not to be construed as limitation of this invention, and that many variations may be resorted to without departing from the spirit and scope of this invention. In this specification, "g." and "m." are "gram(s)" and "milliliter(s)" respectively. Temperatures are all uncorrected, and percentages are all on the weight basis.

EXAMPLE 1

1. A mixture of 10 g. of androst-4-en-3-one, 40 ml. of dioxane, 15 ml. of ethyl orthoformate and 1 g. of paratoluenesulfonic acid is stirred at room temperature for 30 minutes, after which time 1 ml. of pyridine is added. The reaction mixture is poured into water and extracted with ether.

The ether layer is washed with water and dried with anhydrous sodium sulfate, followed by concentration of the solvent under reduced pressure. The procedure yields 8.5 g. of 3-ethoxyandrosta-3,5-diene. Recrystallized from methanol. Melting point: 95°–96°C.

Elemental analysis for $C_{21}H_{32}O$: Calcd. C, 83.94; H, 10.73; Found C, 84.34; H, 10.72.

$UV\lambda_{max}^{Ethanol}$ : 240 m$\mu$ ($\epsilon$ : 19500)

2. In a mixture of 30 ml. of ethylene chloride and 0.4 ml. of pyridine is dissolved 5 g. of 3-ethoxyandrosta-3,5-diene according to (1). Separately, there are prepared two solutions, one being a solution of 5.25 ml. of freshly distilled phosphorus oxychloride in 15 ml. of ethylene chloride and the other being a solution of 75 ml. of dehydrated dimethylformamide in 10 ml. of ethylene chloride. The solution of phosphorus oxychloride is cooled to 0°–5°C and, under stirring, the solution of dimethylformamide is added dropwise over a period of 30 minutes. To this solution is promptly added the solution of 3-ethoxyandrosta-3,5-diene previously prepared. The mixture is stirred for 1 hour, after which a 5 % aqueous solution of sodium acetate is added. The mixture is stirred vigorously for 10 minutes. The reaction mixture is then extracted with ether, washed with water, dried with anhydrous sodium sulfate and concentrated. The procedure yields 3 g. crystals of 3-ethoxy-6-formylandrosta-3,5-diene. Recrystallized from ethanol. Melting point: 116°–118°C.

Elemental analysis for $C_{22}H_{32}O_2$: Calcd. C, 80.44; H, 9.83; Found C, 79.95; H, 9.83.

$UV\lambda_{max}^{Ethanol}$: 220 m$\mu$ ($\epsilon$ : 10150), 323 m$\mu$ ($\epsilon$ = 15300).

3. In 30 ml. of ethanol are dissolved 1 g. of 3-ethoxy-6-formylandrosta-3,5-diene according to reaction (2), and while the solution is stirred at room temperature, 0.1 g. of sodium borohydride is added. After 20 minutes, the reaction mixture is poured into water and extracted with ether. Then, the extract is washed with water and dried with anhydrous sodium sulfate. Finally the solvent is concentrated, whereupon 1 g. of 3-ethoxy-6-hydroxymethylandrosta-3,5-diene is obtained as an oil.

$UV\lambda_{max}^{Ethanol}$: 254 m$\mu$

4. In 10 ml. of 80 % acetic acid is dissolved 1 g. of 3-ethoxy-6-hydroxymethylandrosta-3,5-diene as obtained by reaction (3), and the resultant solution is heated at 85°C for 30 minutes. The reaction mixture is poured into water, extracted with ether, and washed with an aqueous solution of sodium hydrogen carbonate and water in that order. It is then dried with anhydrous sodium sulfate and concentrated. The procedure yields 0.7 g. of 6-methylenedandrost-4-en-3-one. Recrystallized from n-hexane. Melting point: 95°–96°C.

Elemental analysis for $C_{20}H_{23}O$: Calcd. C, 84.45; H, 9.92; Found C, 84.75; H, 9.95.

$UV\lambda_{max}^{Ethanol}$: 258 m$\mu$ ($\epsilon$ : 10900)

5. In 20 ml. of ethanol is dissolved 1 g. of 6methyleneandrost-4-en-3-one and, then, 0.05 g. of 5 % palladium-on-carbon and 0.5 g. of sodium acetate are added. To this solution under stirring on reflux, 5 ml. of a 1 % ethanolic solution of cyclohexene is added dropwise over a period of 1 hour. After the end-point of the reaction has been confirmed by ultraviolet monitoring, the catalyst is filtered off and the filtrate is concentrated under reduced pressure. Following the addition of water, the concentrate is extracted with ether and the extract is washed with water, dried with anhydrous sodium sulfate and concentrated. The procedure yields 0.8 g. of 6-methylandrosta-4,6-dien-3-one. Recrystallized from n-hexane. Melting point: 95°–96°C Elemental analysis for $C_{20}H_{23}O$: Calcd. C, 84.45; H, 9.92; Found C, 84.44; H, 9.89.

$UV\lambda_{max}^{Ethanol}$: 288 m$\mu$ ($\epsilon$ : 20000)

EXAMPLE 2

1. To a solution of 3.5 g. of androst-4-en-3-one dissolved in 40 ml. of dioxane is added 2.8 g. of dichlorodicyanobenzoquinone, and the mixture is refluxed for 5 hours. After cooling, undissolved material is separated by filtration and, to the filtrate is added 40 ml. of a 10 % aqueous solution of potassium hydroxide, followed by extraction with chloroform. The chloroform layer is washed with an aqueous solution of 5 % sodium bicarbonate, and then washed with water, followed by drying with anhydrous sodium sulfate. The resultant solution is subjeced to the distillation of the solvent to give 2.8 g. of androsta-1,4-dien-3-one.

2. To a solution of 7.0 g. of trimethylsulfoxonium iodide dissolved in 50 ml. of anhydrous dimethylsulfoxide is added 0.7 g. of sodium hydride under cooling at 5°C, followed by stirring for 30 minutes. To the reaction solution is added 2.5 g. of androsta-1, 4-dien-3-one obtained in above (1) and the mixture is stirred for 7 days at room temperature. To the reaction mixture is added 150 ml. of 1N hydrochloric acid, and the mixture is extracted with chloroform. The extract is washed with saturated aqueous solution of sodium bicarbonate and water in this order and dried with anhydrous sodium sulfate, followed by the distillation of the solvent. The residue is dissolved in 20 ml. of benzene and the solution is poured onto a column packed with silica gel, and then adsorbed material is eluted with a mixed solvent of benzene-ether (5:1).

The procedure gives 0.6 g. of 1$\alpha$,2-methyleneandrost-4-en-3-one.

3. A mixture of 10 g. of 1$\alpha$,2-methyleneandrost-4-en-3-one, 40 ml. of dioxane, 15 ml. of ethyl orthoformate and 1 g. of para-toluenesulfonic acid is stirred at room temperature for 60 minutes, after which time 1 ml. of pyridine is added. The reaction mixture is extracted with ether.

The ether layer is washed with water and dried with anhydrous sodium sulfate, followed by concentration of the solvent under reduced pressure. The procedure yields 4.5 g. of 3-ethoxy-1$\alpha$,2-methyleneandrosta-3,5-diene.

4. In a mixture of 30 ml. of ethylene chloride and 0.4 ml. of pyridine is dissolved 4.5 g. of 3-ethoxy-1$\alpha$,2-methyleneandrosta-3,5-diene obtained in (3) above. Separately, there are prepared two solutions, one being a solution of 5.25 ml. of freshly distilled phosphorus oxychloride in 15 ml. of ethylene chloride and the other being a solution of 75 ml. of dehydrated dimethylformamide in 10 ml. of ethylene chloride. The solution of phosphorus oxychloride is cooled to 0°–5°C and, under stirring, the solution of dimethylformamide is added dropwise over a period of 30 minutes. To this solution is promptly added the solution of 3-ethoxy-1$\alpha$,2-methyleneandrosta-3,5-diene previously prepared. The mixture is stirred for 1 hour, after which a 5 % aqueous solution of sodium acetate is added. The mixture is stirred vigorously for 10 minutes. The reaction mixture is then extracted with ether, washed with water, dried with anhydrous sodium sulfate and concentrated. The procedure yields 3 g. crystals of 3-ethoxy-6-formyl-1$\alpha$,2-methyleneandrosta-3,5-diene.

5. In 30 ml. of ethanol are dissolved 1 g. crystals of 3-ethoxy-6-formyl-1$\alpha$,2-methyleneandrosta-3,5-diene obtained in (4) above, and while the solution is stirred at room temperature, 0.1 g. of sodium borohydride is added. After 20 minutes, the reaction mixture is poured into water and extracted with ether. Then, the extract is washed with water and dried with anhydrous sodium sulfate, followed by the distillation of the solvent, whereupon 0.4 g. of 3-ethoxy-6-hydroxymethyl-1$\alpha$,2-methyleneandrosta-3,5-diene is obtained.

6. In 10 ml. of 80 % acetic acid is dissolved 0.3 g. of 3-ethoxy-6-hydroxymethyl-1$\alpha$,2-methyleneandrosta-3,5-diene as obtained by reaction (5), and the resultant solution is heated at 85°C for 30 minutes. The reaction mixture is poured into water, extracted with ether, and washed with an aqueous solution of sodium hydrogen carbonate and water in that order. It is then dried with anhydrous sodium sulfate and concentrated. The residue is dissolved in 2 ml. of benzene and the solution is poured onto a column packed with silica gel, and then adsorbed material is eluted with a mixed solvent of benzene-ether(10:1). The procedure gives 0.1 g. of 6-methylene-1$\alpha$,2-methyleneandrost-4-en-3-one. Melting point: 195°–196°C 7. In 5 ml. of ethanol is dissolved 0.1 g. of 6-methylene-1α,2-methyleneandrost-4-en-3-one and, then, 0.01 g. of 5 % palladium-on-carbon and 0.05 g. of sodium acetate are added. Under stirring on reflux, 1 ml. of a 1 % ethanolic solution of cyclohexene is added little by little. The catalyst is filtered off and water is added to the filtrate. The resultant solution is extracted with ether and the extract is washed with water, dried with anhydrous sodium sulfate and concentrated. The procedure yields 0.05 g. of crystals of 1α,2-methylene-6-methylandrosta-4,6-dien-3-one. Recrystallized from n-hexane. Melting point: 204°–205°C Elemental analysis for $C_{21}H_{28}O$; Calcd. C, 85.08; H, 9.52; Found C, 85.21; H, 9.55.

EXAMPLE 3

1. A mixture of 0.5 g. of androst-4-en-3-one, 0.25 g. of sodium hydride, 0.5 ml. of ethyl formate and 10 ml. of benzene is stirred at room temperature for 5 hours, after which time the excess sodium hydride is decomposed with methanol. To the reaction mixture is added 50 ml. of water and the mixture is extracted with ether. The aqueous layer is adjusted to pH 2 to 3 with dilute hydrochloric acid and then extracted with ether. The ether layer is washed with water and dried, followed by distillation of ether, whereby 0.4 g. of oily yellow material is obtained. The material is dissolved in 20 ml. of acetone and are added to the solution 0.6 g. of potassium carbonate and 2 ml. of methyl iodide, followed by refluxing for 2 hours. The reaction solution is concentrated under reduced pressure. To the concentrated solution is added 50 ml. of water and the mixture is extracted with ether. The extract is washed with water and dried with unhydrous sodium sulfate, followed by the concentration to give oily material. The oily material is dissolved in about 10 ml. of ethanol and to the ethanol solution is added 0.3 g. of sodium ethoxide, followed by leaving at room temperature as it is overnight. To the solution is added 100 ml. of water and the resultant mixture is extracted with ether, followed by washing with water. After drying with unhydrous sodium sulfate, the ether solution is subjected to the distillation of solvent to give about 0.2 g. of 2α-methylandrost-4-en-3-one.

2. By a procedure similar to (3), (4), (5), (6) and (7) in Example 2, 0.53 g. of 2α,6-dimethylandrost-4-6-diene 3-one is obtained from 5 g. of 2α-methylandrost-4-en-3-one as oily material.

IR $\gamma_{max}^{neat}$ cm$^{-1}$ : 1660, 1620, 1580, 1235, 1228, 1108, 885, 875, 730.

UV $\lambda_{max}^{EtOH}$ mμ : 288.

NMR $\delta_{ppm}^{CDCl_3}$ : 0.78(3H,s), 1.1(3H,s), 1.14(3H,d,J=6Hz), 1.83(3H,d,J=0.5Hz), 5.82(1H,s), 5.98(1H,broad s).

What is claimed is:

1. A compound of the formula

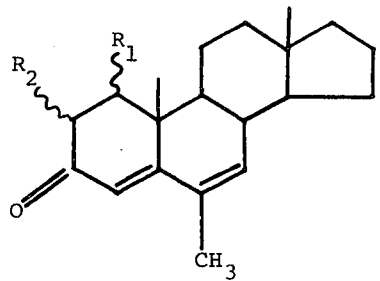

wherein each of $R_1$ and $R_2$ represents hydrogen or methyl or $R_1$ and $R_2$ may be combined to form the methylene group.

2. 6-Methylandrosta-4,6-dien-3-one.
3. 2α,6-Dimethylandrosta-4,6-dien-3-one.
4. 1α,2-Methylene-6-methylandrosta-4,6-dien-3-one.

* * * * *